United States Patent
Lorenzo

(10) Patent No.: US 10,806,461 B2
(45) Date of Patent: *Oct. 20, 2020

(54) IMPLANTABLE MEDICAL DEVICE DETACHMENT SYSTEM WITH SPLIT TUBE

(71) Applicant: DePuy Synthes Products, Inc., Raynham, MA (US)

(72) Inventor: Juan Lorenzo, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 205 days.

This patent is subject to a terminal disclaimer.

(21) Appl. No.: 15/964,857

(22) Filed: Apr. 27, 2018

(65) Prior Publication Data

US 2019/0328398 A1  Oct. 31, 2019

(51) Int. Cl.
*A61B 17/12* (2006.01)
*A61M 25/00* (2006.01)

(52) U.S. Cl.
CPC ... *A61B 17/12022* (2013.01); *A61M 25/0054* (2013.01); *A61M 25/0074* (2013.01);
(Continued)

(58) Field of Classification Search
CPC .... A61B 17/12022; A61B 2017/12054; A61B 17/1214; A61B 2017/1205; A61B 17/12113; A61B 2017/00526; A61B 17/12109; A61B 2017/00309; A61B 2017/00477; A61B 2017/00862; A61B 2017/00867; A61B 2017/00951;
(Continued)

(56) References Cited

U.S. PATENT DOCUMENTS

| 3,429,408 A | 2/1969 | Maker |
| 5,250,071 A | 10/1993 | Palermo |

(Continued)

FOREIGN PATENT DOCUMENTS

| EP | 1 985 244 A2 | 10/2008 |
| EP | 3 092 956 A1 | 11/2016 |
| EP | 3 501 427 A1 | 6/2019 |

OTHER PUBLICATIONS

"Weld Types Explained!" accessed from WC Welding, <https://www.wcwelding.com/joint-types.html> published Feb. 16, 2014 (Year: 2014).*

(Continued)

*Primary Examiner* — Katherine M Shi
(74) *Attorney, Agent, or Firm* — Troutman Pepper Hamilton Sanders LLP

(57) ABSTRACT

A detachment system for delivering an implantable medical device to a target location of a body vessel has a generally hollow distal tube. The distal tube includes a proximal end, a distal end, and a compressible portion of the tube itself, between the proximal and distal ends which is axially movable from a compressed to an elongated condition. A generally hollow proximal tube has a proximal end and a distal end. An engagement system engages and deploys the implantable medical device engaged at the distal end of the distal tube. The engagement system moves the compressible portion to the compressed condition when engaging the implantable medical device, and deploys the implantable medical device and releases the compressible portion to the elongated condition.

15 Claims, 5 Drawing Sheets

(52) U.S. Cl.
CPC .............. *A61B 2017/12054* (2013.01); *A61M 2025/0079* (2013.01)

(58) Field of Classification Search
CPC ...... A61F 2002/9505; A61F 2002/9511; A61F 2/95; A61M 25/0054; Y10T 29/49826
See application file for complete search history.

(56) References Cited

U.S. PATENT DOCUMENTS

| | | | |
|---|---|---|---|
| 5,569,221 A | 10/1996 | Houser et al. | |
| 6,391,037 B1 | 5/2002 | Greenhalgh | |
| 6,561,988 B1* | 5/2003 | Turturro | A61B 10/0266 600/564 |
| 8,062,325 B2 | 11/2011 | Mitelberg et al. | |
| 9,155,540 B2 | 10/2015 | Lorenzo | |
| 9,232,992 B2 | 1/2016 | Heidner | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,120 B2 | 5/2017 | Lagodzki et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman | |
| 9,770,577 B2 | 9/2017 | Li | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman | |
| 9,833,252 B2 | 12/2017 | Sepetka | |
| 9,833,604 B2 | 12/2017 | Lam | |
| 9,833,625 B2 | 12/2017 | Waldhauser et al. | |
| 10,517,604 B2 | 12/2019 | Bowman et al. | |
| 2006/0064151 A1 | 3/2006 | Guterman | |
| 2008/0027561 A1 | 1/2008 | Mitelberg et al. | |
| 2008/0045997 A1* | 2/2008 | Balgobin | A61B 17/12022 606/200 |
| 2008/0097462 A1* | 4/2008 | Mitelberg | A61F 2/95 606/108 |
| 2008/0281350 A1 | 11/2008 | Sepetka | |
| 2009/0312748 A1 | 12/2009 | Johnson et al. | |
| 2010/0114017 A1* | 5/2010 | Lenker | A61B 17/12118 604/96.01 |
| 2010/0324649 A1 | 12/2010 | Mattsson | |
| 2012/0035707 A1 | 2/2012 | Mitelberg et al. | |
| 2012/0283768 A1 | 11/2012 | Cox et al. | |
| 2014/0058435 A1 | 2/2014 | Jones et al. | |
| 2014/0135812 A1 | 5/2014 | Divino et al. | |
| 2014/0200607 A1 | 7/2014 | Sepetka et al. | |
| 2015/0230802 A1 | 8/2015 | Lagodzki et al. | |
| 2015/0335333 A1 | 11/2015 | Jones et al. | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu | |
| 2017/0027640 A1 | 2/2017 | Kunis et al. | |
| 2017/0027692 A1 | 2/2017 | Bonhoeffer | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero | |
| 2017/0079680 A1 | 3/2017 | Bowman | |
| 2017/0079766 A1 | 3/2017 | Wang | |
| 2017/0079767 A1 | 3/2017 | Leon-Yip | |
| 2017/0079812 A1 | 3/2017 | Lam et al. | |
| 2017/0079817 A1 | 3/2017 | Sepetka | |
| 2017/0079819 A1 | 3/2017 | Pung et al. | |
| 2017/0079820 A1 | 3/2017 | Lam et al. | |
| 2017/0086851 A1 | 3/2017 | Wallace | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Grandfield | |
| 2017/0100183 A1 | 4/2017 | Iaizzo | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein | |
| 2017/0165454 A1 | 6/2017 | Tuohy | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0245885 A1* | 8/2017 | Lenker | A61B 17/3478 |
| 2017/0252064 A1 | 9/2017 | Staunton | |
| 2017/0258476 A1 | 9/2017 | Hayakawa et al. | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh | |
| 2017/0303942 A1 | 10/2017 | Greenhalgh et al. | |
| 2017/0303947 A1 | 10/2017 | Greenhalgh | |

(56) References Cited

U.S. PATENT DOCUMENTS

| | | |
|---|---|---|
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |

OTHER PUBLICATIONS

Extended European Search Report issued in corresponding European Patent Application No. 19 17 1368 dated Sep. 18, 2019.

\* cited by examiner

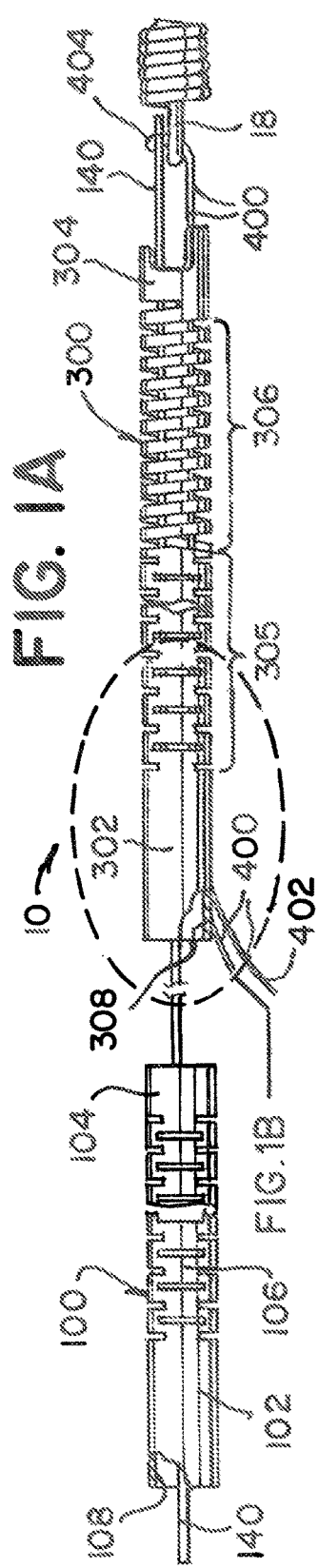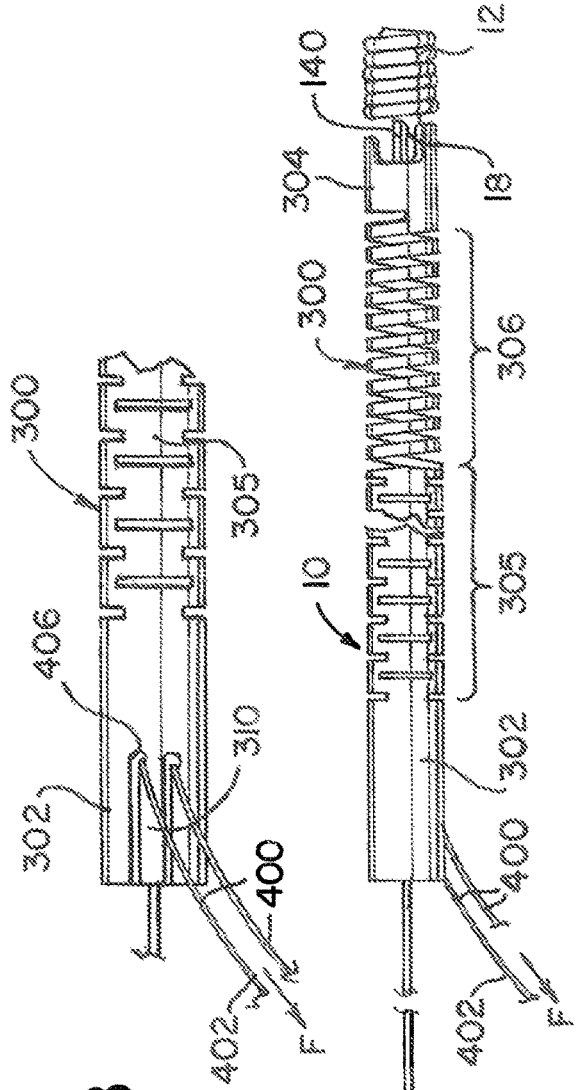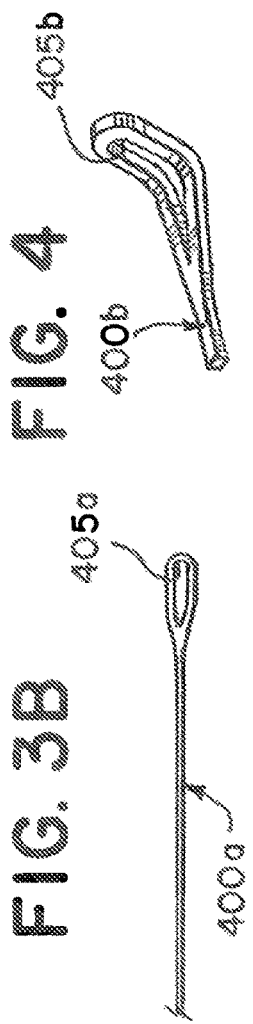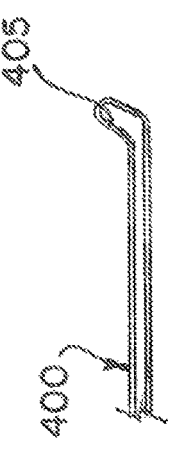

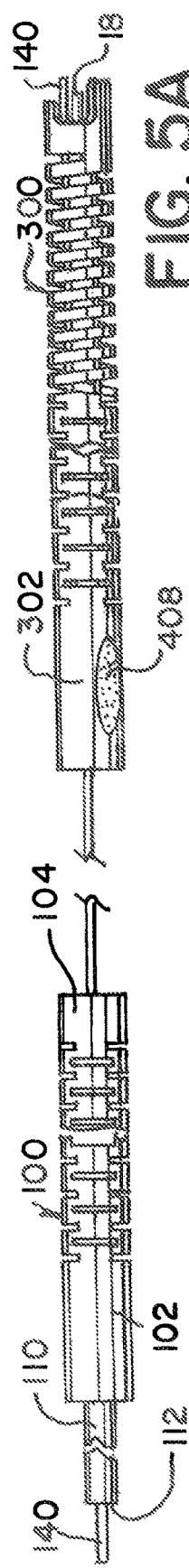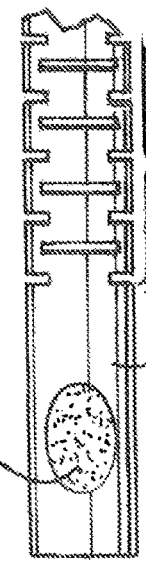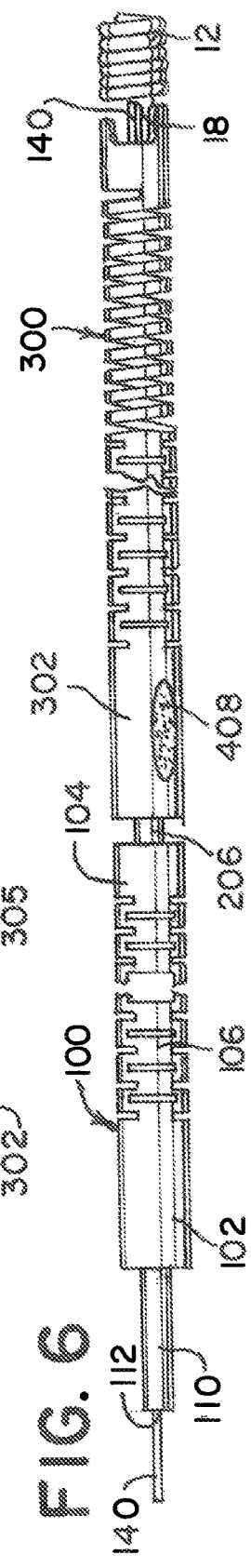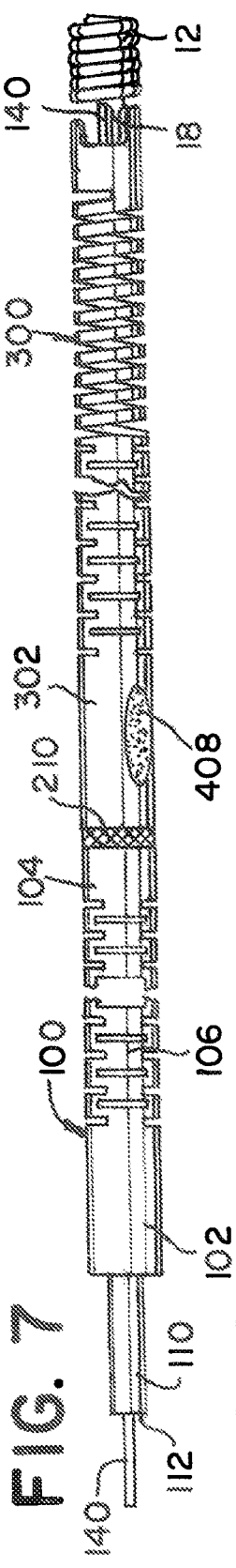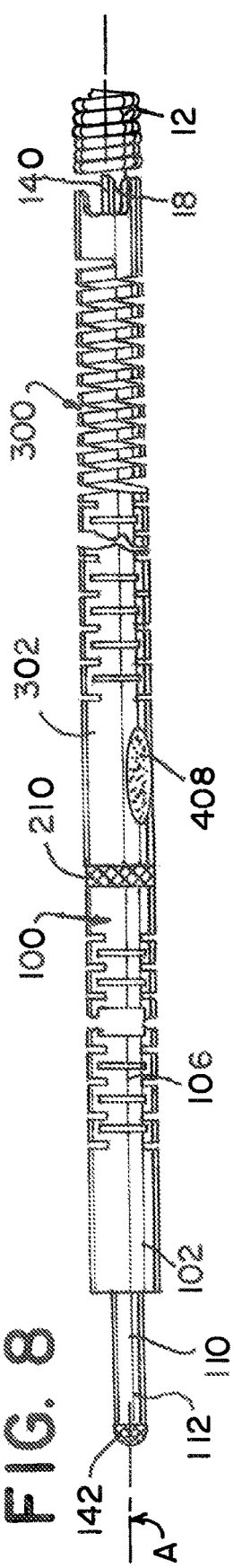

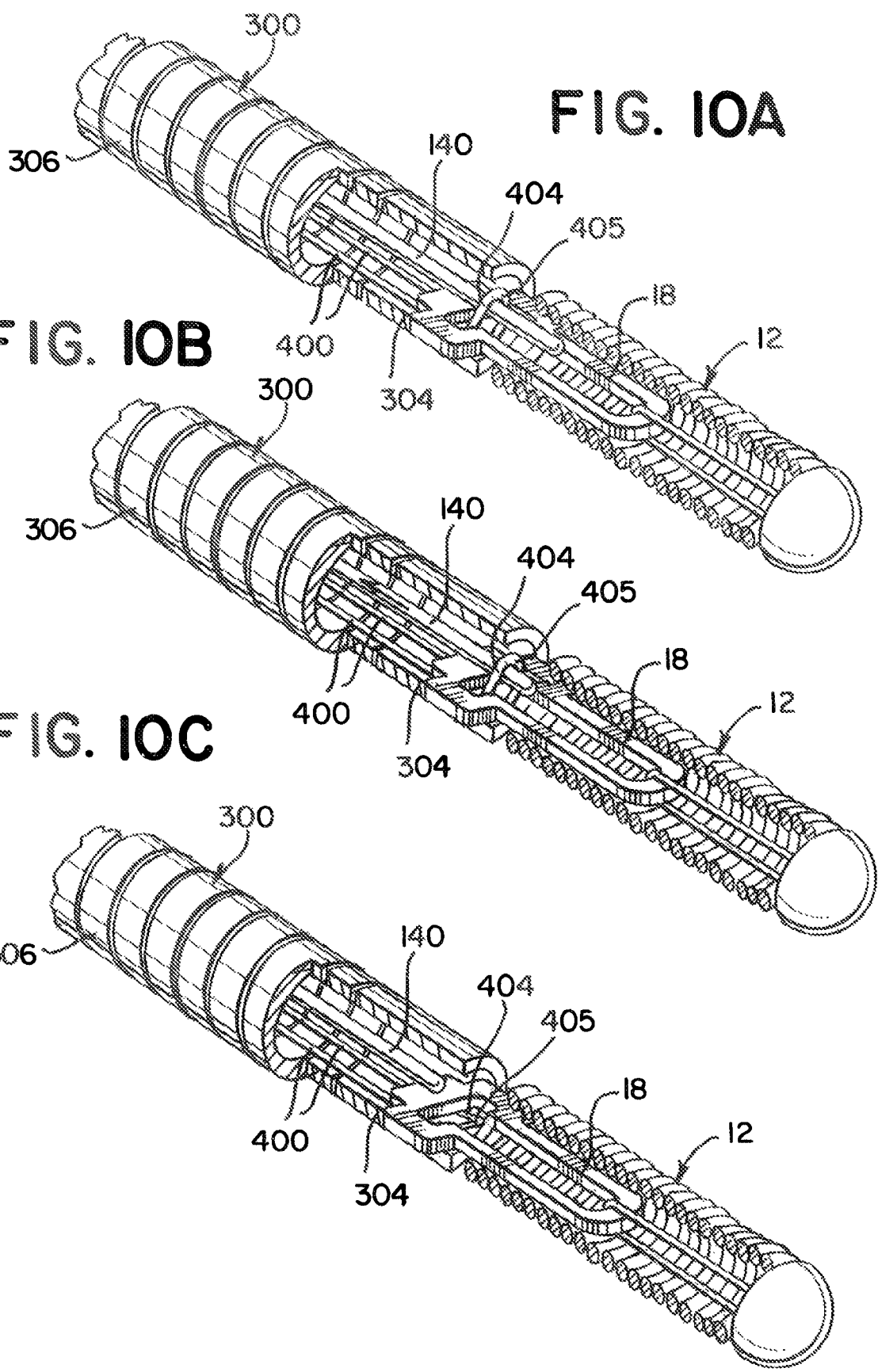

IMPLANTABLE MEDICAL DEVICE DETACHMENT SYSTEM WITH SPLIT TUBE

FIELD OF THE INVENTION

This invention generally relates to interventional medical device systems that are navigable through body vessels of a human subject. More particularly, this invention relates to detachment systems for deploying an implantable medical device to a target location of a body vessel and methods of using the same.

BACKGROUND

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, especially for example brain tissue, it is very difficult and often risky to perform surgical procedures to treat defects of the cranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the coil through the catheter and out of the distal end of the catheter into the delivery site. Some of the problems that have been associated with these procedures relate to ensuring the complete release and deployment of the coil. For example, U.S. Pat. No. 5,250,071 to Palermo, which is hereby incorporated herein by reference, describes a detachment system whereby interlocking clasps of the system and the coil are held together by a control wire. The control wire is moved proximally to disengage the clasps from each other. However, the system does not include any positive means for separating the disengaged clasps from each other, so merely retracting the control wire does not ensure release and deployment of the coil. Numerous other detachment systems currently in use suffer from similar problems.

In addition, U.S. Pat. No. 8,062,325 discloses a single tubular carrier to deliver and deploy the vascular occlusion device, but has only a single compressible section. Therefore, a need remains for a more rapid release detachment system or method that can ensure release and deployment of an implantable medical device. Further advantages could be realized with a detachment system or method incorporating a simple and inexpensive locking and deployment system.

SUMMARY

A detachment system delivers an implantable medical device to a target location of a body vessel with a generally hollow distal tube. The distal tube has a proximal end, a distal end, and a compressible portion of the distal tube itself axially movable from a compressed condition to an elongated condition, between the proximal and distal ends. Also includes is a generally hollow proximal tube having a proximal end and a distal end, the proximal and distal tubes are joined, and an engagement system engaging and deploying the implantable medical device engaged at the distal end of the distal tube. The engagement system moves the compressible portion to the compressed condition when engaging the implantable medical device, and deploys the implantable medical device and releases the compressible portion to the elongated condition.

In another example, the engagement system can be removably fixed to the proximal end of the distal tube when engaging the implantable medical device to maintain the compressed condition. Also, the engagement system can be removably fixed to the proximal end of the proximal tube when engaging the implantable medical device.

An example of the engagement system has a locking member and a loop wire. When the loop wire interacts with the locking member to engage the implantable medical device, a force on the loop wire moves the compressible portion to the compressed condition, and the loop wire is welded to the proximal end of the distal tube to removably fix the engagement system. A force on the locking member releases the loop wire, disengages the implantable medical device, and allows the compressible portion to return the elongated condition.

Other examples have the compressible portion of the distal tube as a spiral-cut portion of the distal tube. The compressible portion can be adapted to deploy the implantable medical device engaged by the engagement system when the compressible portion moves to the elongated condition. Further, the compressible portion of the distal tube is adapted to automatically/resiliently move to the elongated condition when the engagement system is disengaged from the implantable medical device. The proximal tube can also include a flexible portion of the proximal tube itself, between the proximal and distal ends which is flexible, and the distal tube can comprise a flexible portion of the distal tube itself, between the proximal end and the compressible portion, which is flexible.

A method of detaching an implantable medical device, using the examples above can include the steps of forming a compressible portion on the distal tube between the proximal and distal ends, engaging the implantable medical device with an engagement system, applying a force to the engagement system to compress the compressible portion, fixing the engagement system to the distal tube to maintain a compressed state, and joining the distal tube and proximal tube together. As above, the engagement system can be removably fixed to the proximal end of the distal tube.

The detachment method example can further have the step of removably fixing the engagement system to the proximal end of the proximal tube when engaging the implantable medical device. The engagement step can include the step of using the loop wire with the locking member to engage the implantable medical device; and the applying step further comprises the step of applying force to the loop wire to move the compressible portion to the compressed condition. Other example steps include applying a force on the locking member, disengaging the implantable medical device, and allowing the compressible portion to return the elongated condition.

Examples of the forming step can include the step of spiral-cutting a portion of the distal tube and the further have the step of deploying the implantable medical device engaged by moving the compressible portion to the elongated condition. Additionally, the compressible portion of the distal tube can be adapted to automatically/resiliently move to the elongated condition when the engagement system is disengaged from the implantable medical device.

Further, the joining step further has the steps of welding the proximal tube to the distal tube at the weld band.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1A is an exploded view of an example of the detachment system of the present invention with the medical device partially disengaged;

FIG. 1B is a magnified view of FIG. 1A;

FIG. 2 is an exploded view of an example of the detachment system of the present invention with the medical device engaged;

FIG. 3A is a side perspective view of an example of a loop wire according to an example;

FIG. 3B is a plan view of an example of a loop wire according to another example;

FIG. 4 is a front perspective detail view of an opening of the loop wire in an up-turned condition in an alternate example;

FIG. 5A is an exploded view of an example of the detachment system of the present invention with the medical device engaged and the loop wire secured;

FIG. 5B is a magnified view of the loop wire secured to the distal tube;

FIG. 6 is a plan view of a gap between the proximal and distal tubes;

FIG. 7 is a plan view of the proximal and distal tubes welded together;

FIG. 8 illustrates the proximal weld at the small tube;

FIGS. 10A-10D illustrate the medical device being detached with a partial cross-section;

DETAILED DESCRIPTION

Figure 9:
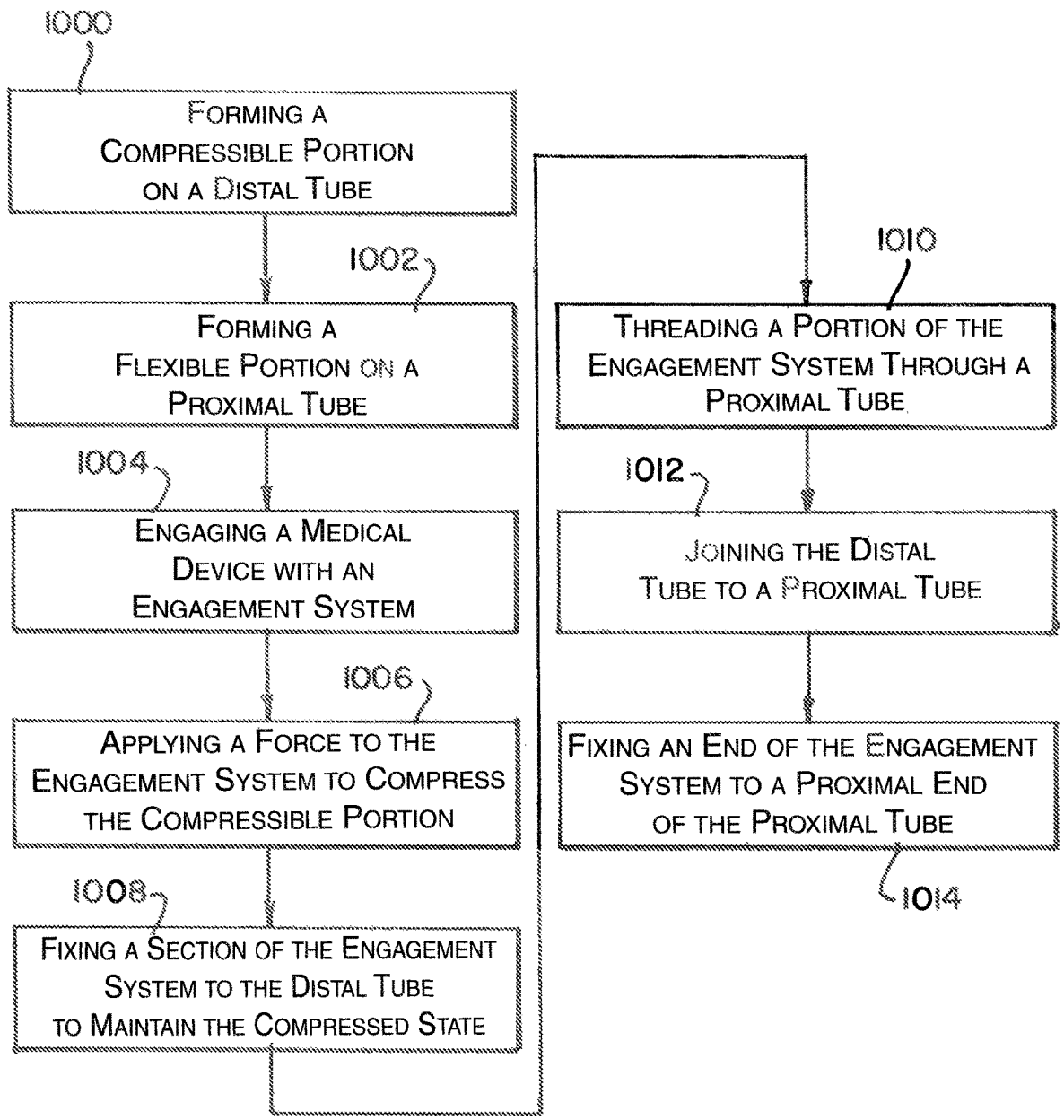
FIG. 9 illustrates an example method of forming the detachment system of the present invention.

The figures illustrate a generally hollow or tubular structure according to the present invention. When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

An example of a detachment system 10 of the present invention, as illustrated in FIGS. 1A, 1B, and 2, can have a proximal elongated delivery hypotube assembly 100 and a distal delivery tube 300. An implantable medical device 12 is engaged at one end of the distal delivery tube 300. The implantable medical device 12 can be an embolic coil, but it will be appreciated that virtually any implantable medical device 12 may be delivered and deployed by the detachment system 10 according to the present invention. The medical device 12 is engaged to the system using a locking member 140 and a loop wire 400. The medical device 12 has a locking portion 18 to interface with an engagement system 140, 400.

The proximal delivery tube 100 can have a proximal end portion 102, distal end portion 104, and a flexible portion 106 in between. The proximal delivery tube 100 forms an axial lumen 108 therein. The proximal end 102 engages with a smaller diameter tube 110 (see FIGS. 5A, 6-8) along the axial lumen 108. The distal delivery tube 300 can have a proximal end portion 302, distal end portion 304, and between the two, a compressible portion 306. In one example, the compressible portion 306 can be closer to the distal end portion 304, and between the proximal end portion 302 and the compressible portion 306 can be a flexible portion 305. The distal delivery tube 300 forms an axial lumen 308 therein.

The delivery tubes 100, 300 can be made of a biocompatible material, such as stainless steel. The tubes 100, 300 can typically have a diameter of between about 0.010 inch and about 0.018 inch, a preferred tube having a diameter of approximately 0.0145 inch. These examples of tube size are suitable for delivering and deploying embolic coils to target locations, typically aneurysms, within the neurovasculature. Differently sized tubes 100, 300 comprised of other materials may be useful for different applications and are within the scope of the present invention.

The flexible portions 106, 305 allow the delivery tubes 100, 300 to bend and flex. This assists tracking the system 10 through the catheter and the tortuous path through the human vasculature. The flexible portions 106, 306 can be formed with interference spiral cuts. These cuts allow for gaps to permit bending but in one example, do not act as a spiral-cut spring. Thus, can bend and flex but do not compress.

The compressible portion 306 is axially adjustable between an elongated condition and a compressed condition. Preferably, the compressible portion 306 is formed from a spiral-cut portion of the tube 300, formed by a laser-cutting operation. However, any other arrangement allowing axial adjustment (e.g., a wound wire or spiral ribbon) is also suitable for use with detachment systems according to the present invention. Most preferably, the compressible portion 306 is in the elongated condition at rest and automatically or resiliently returns to the elongated condition from a compressed condition, unless otherwise constrained. The function of the compressible portion 306 is described in greater detail herein.

FIGS. 3A, 3B, and 4 illustrate examples of the loop wire 400. The loop wire 400 can be relatively small, having the thickness of a hair in some embodiments, so it may be preferred for it to be entirely shielded by the distal end 304 of the distal delivery tube 300 to prevent damage from accidental contact. The loop wire 400 can be an elongated wire that is looped, as in FIG. 3A. The loop wire 400a can also be a single elongated wire with an opening 405, as illustrated in FIG. 3B. The opening 405 can be formed by loosely bending the loop wire 400a in half. In an alternative example, the loop wire 400b comprises a flat ribbon defining an opening 405a at a distal portion and the opening 405b can be in an up-turned condition suitable for engaging an end of the implantable medical device 12. An example of the loop wire 400, 400a, 400b can be elastically deformable to the up-turned condition such that it will return to the substantially flat condition when not otherwise constrained. The loop wire 400, 400a, 400b may be formed from of any of a number of materials, including nitinol and stainless steel.

To load the detachment system 10, the locking member 140 is inserted axially within the lumens 108, 208, 308 of both tubes 100, 300. A distal end 404 of the loop wire 400 is inserted into the distal delivery tube 300 through an anchor portion 310 located on the proximal end 302 of the distal tube 300 and passed through the lumen 308 to the distal end 304. The distal end of the loop wire 404 can then be looped to form the opening 405. The opening 405 is passed through the locking portion 18 and the locking member 140 is passed through the opening 405 to engage the medical device 12. See, FIGS. 1A and 11.

Figure 11:
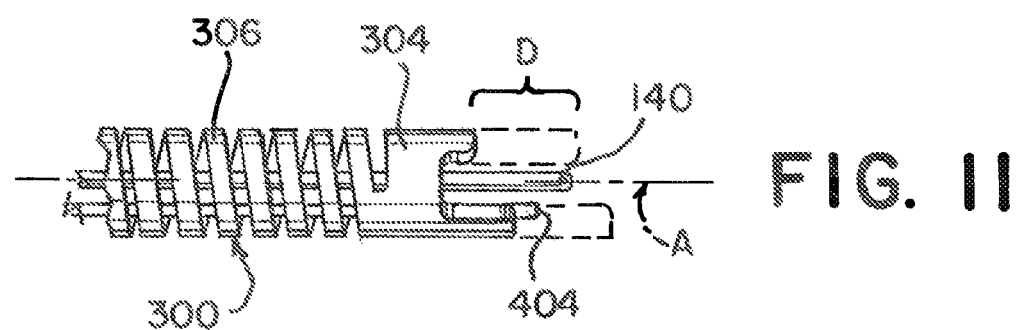
FIG. 11 is a side view of an example of the distal tube in the compressed and expanded state.

The loop wire 400 is pulled taught at a proximal end of the loop wire 402 and continued force F compresses the compressible portion 306. The amount of compression can be controlled by the amount of force F applied to the proximal end 402 of loop wire 400 after the medical device 12 is mounted on the distal end 304 of the distal tube 300. FIGS. 2 and 11 illustrate the mounted medical device 12 and the distal tube 300 in a compressed state. Once the distal tube 300 is compressed the appropriate amount, the loop wire 400 is anchor welded 408 at wire weld point 406 (between the proximal 402 and distal 404 ends) to the proximal end 302 (i.e. behind the compressible portion 306) at or approximate to the anchor portion 310 of the distal delivery tube 300. See, FIGS. 5A and 5B. The level of compression of the distal delivery tube 300 is adjusted by varying the amount of force F on the loop wire 400 prior to securing the loop wire 400 in place with the anchor weld 408.

FIGS. 6 and 7 illustrate the joining of the proximal delivery tube 100 and the distal delivery tube 300. FIG. 6 illustrates the distal end 104 of the proximal tube 100 being pulled toward, and in some examples, contacting the proximal end 302 of the distal tube 300. The proximal and distal tubes 100, 300, in this example, do not come into contact, but leave the weld band 206 as a gap. The two tubes 100, 300 are then circumferentially welded 210 together at the weld band 206 to form a unitary device 10.

Prior to welding of the two tubes, 100, 300, the locking member 140 (as discussed above) is pulled through the proximal tube lumen 108 through to the small tube 110. At a proximal opening 112 in the small tube 110, opposite the proximal end 102 of the proximal tube 100, the locking member 140 is welded 142 to the small tube 110. This is illustrated in FIG. 8.

FIG. 9 illustrates an example of a method of assembling the detachment system 10. The method includes forming the compressible portion 306 on the distal tube 300 (step 1000) and forming the flexible portion 106 on the proximal tube 100 (step 1002). Step 1002 can also include forming the flexible portion 305 on the distal tube 300. The compressible portion 306 can be formed by spiral cutting the distal tube 300 or by any other means to form a tube that can be compressed and then return to its uncompressed state quickly. The flexible portion 106 of the proximal tube 100 can be interference cut or by any other means to increase the flexibility of the proximal tube 100. Once at least the distal tube 300 is ready, the medical device 12 can be engaged with an engagement system 140, 400 (step 1004) and a force F can be applied to the engagement system 140, 400 to compress the compressible portion 306 (step 1006). Here it is noted that while an example is presented above using the locking member 140 and the loop wire 400 as an engagement system, one of ordinary skill can realize different methods to secure the medical device 12 while still applying releasable force on the compressible portions 306 to be released when the engagement system 140, 400 is disengaged from the medical device 12. A section 406 of the engagement system 140, 400 is then engaged to the distal tube 300 to maintain the compressed state of the compressible portion 306 (step 1008). A portion of the engagement system 140, 400 is threaded through the proximal tube 100 (step 1010). The distal 300 and proximal tubes 100 are joined together (step 1012). Here, in this example, the ends 104, 302 of the tubes 100, 300 are welded together 210. The end of the engagement system 140, 400 can then be joined to a proximal end 102 of the proximal tube 100 (step 1014) to complete the device 10.

Figure 10D:
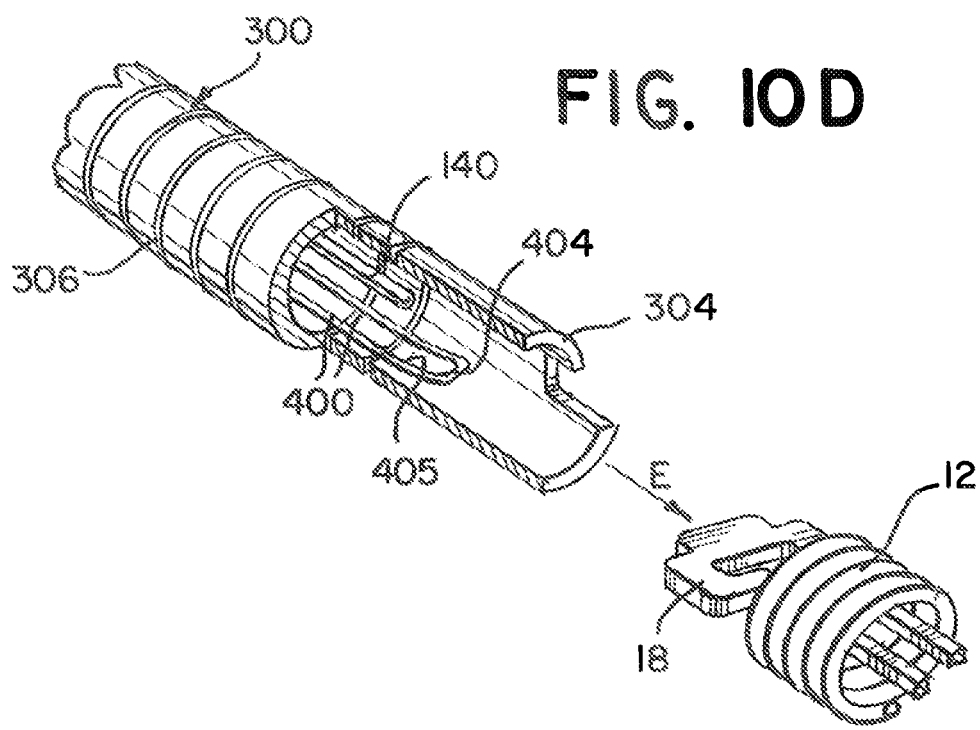

Turning to FIGS. 10A-10D, the detachment of the medical device 12 is illustrated in more detail. FIG. 10A illustrates the engagement system 140, 400 locked into the locking portion 18 of the medical device 12. The loop wire 400 opening 405 can be placed through the locking portion 18. When the locking member 140 is put through the opening 405 the medical device 12 is now secure. Force F was previously applied to place the distal tube 300 in the compressed state. FIG. 10B illustrates the locking member 140 being drawn proximally to begin the release sequence for the medical device 12. FIG. 10C illustrates the instant the locking member 140 exits the opening 405 and is pulled free of the loop wire 400. The distal end 404 of the loop wire 400 falls away/returns to its preformed shape (as discussed above) and exits the locking portion 18. As can be seen, there is now nothing holding the medical device 12 to the detachment system 10. FIG. 10D illustrates the end of the release sequence. Here, the compressible portion 306 has expanded/returned to its original shape and "sprung" forward. An elastic force E is imparted by the distal end 304 of the distal tube 300 to the medical device 12 to "push" it away to ensure a clean separation and delivery of the medical device 12.

Figure 12:
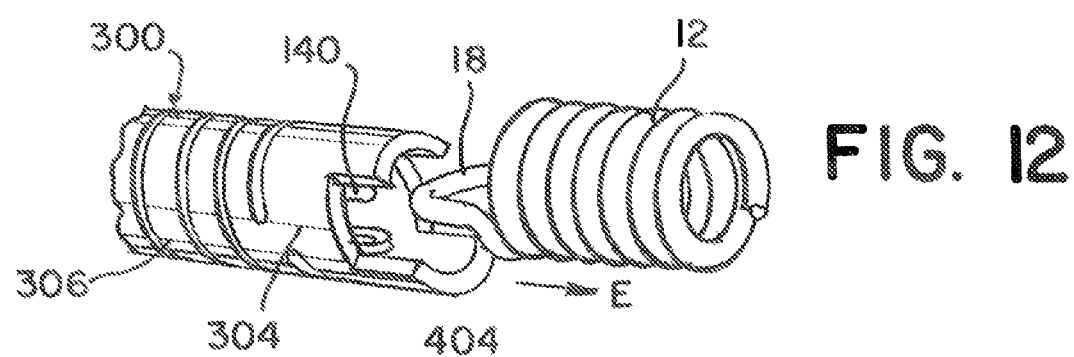
FIG. 12 is a front-side perspective view of an example of the medical device being detached.

FIG. 11 shows the distal tube 300 illustrated without the medical device 12 but with the compressible portion 306 shortened in axial length to the compressed condition. In particular, a distance "D" is illustrated by which the distal tube 300 is axially foreshortened in moving the compressible portion 306 from the elongated condition to the compressed condition. This compression can occur along the axis A. FIG. 12 illustrates another view of the medical device 12 at the point of detachment. The locking member 140 has been pulled proximally so that it separated from the loop wire 400, allowing the medical device 12 to separate as the distal compressed portion 306 expands and furthers separates the medical device 12 from the delivery system 10. The arrow "E" denotes the elastic force "pushing" the medical device 12 away from the distal end 304 to assure a clean separation and delivery to the target site inside the patient. The elastic force E acts in the axis A of the lumen 308 and "pushes" the medical device 12 along the same axis A (see FIGS. 8 and 11).

The descriptions contained herein are examples of embodiments of the invention and are not intended in any way to limit the scope of the invention. As described herein, the invention contemplates many variations and modifications of the inventive delivery and release system for a vascular occlusion device, including numerous configurations, numerous stiffness properties and methods for delivering the same. Also, there are many possible variations in the materials and configurations of the release mechanism. These modifications would be apparent to those having ordinary skill in the art to which this invention relates and are intended to be within the scope of the claims which follow.

What is claimed is:

1. A detachment system for delivering an implantable medical device to a target location of a body vessel, comprising:
    an implantable medical device;
    a generally hollow distal tube comprising:
        a proximal end;
        a distal end;
        a compressible portion of the distal tube itself, between the proximal and distal ends which is axially movable from a compressed condition to an elongated condition; and
        a flexible portion between the proximal end and the compressible portion;
    a generally hollow proximal tube having a proximal end, a distal end, and a flexible portion between the proximal and distal ends;
    a weld disposed between the proximal end of the distal tube and the distal end of the proximal tube, joining the proximal and distal tubes;
    an engagement system engaging and deploying the implantable medical device of the detachment system engaged at the distal end of the distal tube;
    wherein the engagement system moves the compressible portion to the compressed condition when engaging the implantable medical device, and
    wherein the engagement system deploys the implantable medical device and releases the compressible portion to the elongated condition.

2. The detachment system of claim 1, wherein the engagement system comprises:
    a locking member; and
    a loop wire,
    wherein when the loop wire interacts with the locking member to engage the implantable medical device, a force on the loop wire moves the compressible portion to the compressed condition, and
    wherein the loop wire is welded to the proximal end of the distal tube to removably fix the engagement system.

3. The detachment system of claim 2, wherein a force on the locking member releases the loop wire, disengages the implantable medical device, and allows the compressible portion to return the elongated condition.

4. The detachment system of claim 1, wherein the compressible portion of the distal tube is a spiral-cut portion of the distal tube.

5. The detachment system of claim 1, wherein the compressible portion is adapted to deploy the implantable medical device engaged by the engagement system when the compressible portion moves to the elongated condition.

6. The detachment system of claim 1, wherein the compressible portion of the distal tube is adapted to automatically and/or resiliently move to the elongated condition when the engagement system is disengaged from the implantable medical device.

7. The detachment system of claim 1, further comprising:
    a gap between the proximal tube and the distal tube comprises a weld band to weld the proximal tube to the distal tube.

8. The detachment system of claim 1, wherein the proximal end of the distal tube and the distal end of the proximal tube contact each other when welded.

9. A method of detaching an implantable medical device with the system of claim 1, comprising the steps of:
    forming the compressible portion on the distal tube between the proximal and distal ends;
    engaging the implantable medical device with the engagement system;
    applying a force to the engagement system to compress the compressible portion;
    fixing the engagement system to the distal tube to maintain a compressed state;
    welding the proximal end of the distal tube to the distal end the proximal tube together.

10. The detachment method of claim 9, wherein the engagement system comprises a locking member, and a loop wire,
    wherein the engaging step further comprising the step of using the loop wire with the locking member to engage the implantable medical device; and
    wherein the applying step further comprises the step of applying force to the loop wire to move the compressible portion to the compressed condition.

11. The detachment method of claim 10, further comprising the steps of:
    applying a force on the locking member;
    disengaging the implantable medical device; and
    allowing the compressible portion to return the elongated condition.

12. The detachment method of claim 9, wherein the forming step comprises the step of spiral-cutting a portion of the distal tube.

13. The detachment method of claim 9, further comprising the step of deploying the implantable medical device engaged by moving the compressible portion to the elongated condition.

14. The detachment method of claim 9, wherein the compressible portion of the distal tube is adapted to automatically and/or resiliently move to the elongated condition when the engagement system is disengaged from the implantable medical device.

15. The detachment method of claim 9, wherein the welding step further comprises the steps of:
    forming a gap between the proximal tube and the distal tube comprising a weld band; and
    welding the proximal tube to the distal tube at the weld band.

* * * * *